United States Patent
Biehl et al.

(10) Patent No.: US 11,077,023 B2
(45) Date of Patent: Aug. 3, 2021

(54) METHOD FOR PRODUCING A MEDICAL PREPARATION USING A PERISTALTIC PUMP

(71) Applicant: FRESENIUS KABI DEUTSCHLAND GMBH, Bad Homburg (DE)

(72) Inventors: Martin Biehl, St. Wendel (DE); Michael Hock, Münzenberg (DE); Henrik Schaake, Bad Homburg (DE); Martin Bohm, Magdeburg (DE); Ulla Schöbel, Köthen (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 239 days.

(21) Appl. No.: 16/083,984

(22) PCT Filed: Mar. 15, 2017

(86) PCT No.: PCT/EP2017/056106
§ 371 (c)(1),
(2) Date: Sep. 11, 2018

(87) PCT Pub. No.: WO2017/158011
PCT Pub. Date: Sep. 21, 2017

(65) Prior Publication Data
US 2020/0289372 A1    Sep. 17, 2020

(30) Foreign Application Priority Data
Mar. 15, 2016  (EP) ..................................... 16160328

(51) Int. Cl.
*A61J 3/00*  (2006.01)
*A61M 1/16*  (2006.01)
*A61M 1/26*  (2006.01)
*A61M 1/36*  (2006.01)
*F04B 43/12*  (2006.01)
*F04B 53/10*  (2006.01)

(52) U.S. Cl.
CPC ............ *A61J 3/002* (2013.01); *A61M 1/1645* (2014.02); *A61M 1/1668* (2014.02); *A61M 1/262* (2014.02); *A61M 1/267* (2014.02); *A61M 1/3626* (2013.01); *A61J 2200/74* (2013.01); *F04B 43/12* (2013.01); *F04B 53/10* (2013.01)

(58) Field of Classification Search
None
See application file for complete search history.

(56) References Cited

U.S. PATENT DOCUMENTS

| 4,473,173 | A |   | 9/1984  | Degroff |
|-----------|---|---|---------|---------|
| 5,040,699 | A | * | 8/1991  | Gangemi ............... G01G 19/32 222/1 |
| 5,046,569 | A |   | 9/1991  | Von Der Haar |
| 5,228,485 | A |   | 7/1993  | Lewis |
| 5,697,407 | A |   | 12/1997 | Lasonde |
| 2006/0245964 | A1 |   | 11/2006 | Koslov |
| 2013/0189120 | A1 |   | 7/2013  | Nelson |

FOREIGN PATENT DOCUMENTS

WO    WO87/07236    12/1987

\* cited by examiner

*Primary Examiner* — Daphne M Barry
(74) *Attorney, Agent, or Firm* — Occhiuti & Rohlicek LLP

(57) ABSTRACT

The invention relates to a method and a system for synthesizing a medical preparation, a peristaltic pump being used for pumping liquid from a plurality of source containers. According to the invention, micro-amounts are extracted only in the linear region of the peristaltic pump.

18 Claims, 13 Drawing Sheets

METHOD FOR PRODUCING A MEDICAL PREPARATION USING A PERISTALTIC PUMP

CROSS REFERENCE TO RELATED APPLICATIONS

This application is the national phase under 35 USC 371 of international application no. PCT/EP2017/056106, filed Mar. 15, 2017, which claims the benefit of the priority dates of European Application No. 16160328.7 filed Mar. 15, 2016. The contents of the aforementioned applications are incorporated herein by reference in their entireties.

FIELD OF THE INVENTION

The invention relates to a method and an installation for producing a medical preparation, wherein a peristaltic pump is used to transfer liquids from source containers into a target container. The invention relates in particular to a method by which infusion bags and/or syringes are filled for parenteral nutrition, and to an associated installation.

BACKGROUND OF THE INVENTION

Preparations for parenteral nutrition are produced in a patient-specific manner, for example in pharmacies or hospitals. These preparations are mixtures of different basic nutrients, trace elements and vitamins, if appropriate also together with a pharmaceutical, which are transferred individually into an infusion bag. TPN compounders (TPN=total parenteral nutrition) are used for this purpose. Installations known in practice and commercially available, for example the MultiComp® system from Fresenius, comprise a computer-controlled pump unit by means of which the constituents of the composition are transferred from different source containers into a target container located on a balance.

There are strict safety requirements governing the production of medical preparations of this kind. In particular, a high degree of precision in the metering of all the constituents must be ensured.

The target container can be weighed in order to check the metering.

A problem is that that the medical preparations to be produced comprise components with main constituents such as water, fat, sugar and amino acids, which are delivered in quite a large quantity. In addition to these, there are components which comprise, for example, certain vitamins, minerals or also a pharmaceutical, which have to be delivered in a substantially smaller quantity, in particular in the milliliter range. Such constituents are also referred to as micro-quantities.

OBJECT OF THE INVENTION

In light of the above, the object of the invention is to make available a method for producing a medical preparation, in which method, preferably by means of a peristaltic pump, precise metering of the individual constituents of a medical preparation is made possible.

SUMMARY OF THE INVENTION

The object of the invention is achieved by a method as claimed in claim 1 for producing a medical preparation. Preferred embodiments and developments of the invention may be gathered from the subject matter of the dependent claims, the description and the drawings.

The invention relates in the first instance to a method for producing a medical preparation. The invention relates in particular to a method for producing a preparation for parenteral nutrition.

Here, liquids are removed from a plurality of source containers and transferred into a target container. The production is automated, wherein the person using the installation used for the method can input the desired composition in the target container or can select it from a database with a plurality of recipes.

A defined quantity of liquid is removed from the individual source containers in a predetermined sequence, hereinafter also referred to as the "metering step". After all of the metering steps intended for a target container have been completed, a "filling procedure" is by definition concluded.

There may be constituents that are not allowed to come into direct contact or that are only allowed to come into contact in a defined sequence.

As was stated in the introduction, a medical preparation of this kind typically consists of main constituents, which are delivered in a large quantity, and so-called "micro-quantities", which can in particular contain vitamins, minerals or pharmaceutical components.

A "transfer set" designed as a disposable item is preferably used for the transfer and comprises the hose that is inserted into the peristaltic pump. The transfer set moreover comprises attachment hoses for the source containers and an attachment for the target container. Moreover, the transfer set preferably comprises a valve unit by means of which the attachments to the individual source containers can be opened and closed.

Preferably, during each individual metering step, only a single valve leading to a source container is opened at any one time. Thus, liquid is always removed from only one source container.

In addition to the main constituents of the medical preparation and to the micro-quantities, each preparation also has what is called a universal liquid, also referred to as universal ingredient (UI). This liquid is intended to come into direct contact with any other additive without causing an undesired side effect and is used in each preparation in a relatively large quantity, in particular for filling the preparation to the desired total quantity. The universal liquid is in most cases preferably isotonic water.

The peristaltic pump used for the method has a region with a linear characteristic curve and a region with a non-linear characteristic curve.

A region with a linear characteristic curve is understood as the angle region of an impeller in which the pump output, i.e. the volume in relation to the rotation angle of an impeller of the peristaltic pump, is constant. The delivered volume is proportional to the rotation angle of the pump.

There is a suction-side linear region. This is the region in which a suction-side roller of the peristaltic pump is in engagement with the hose and no other roller comes into engagement with the hose. In the suction-side linear region, the rotation angle is proportional to the delivered volume on the suction side.

There is also a pressure-side linear region in which the rotation angle is proportional to the volume delivered on the pressure side. The pressure-side roller of the peristaltic pump is in this case in engagement with the hose, and no roller disengages from the hose.

It will be appreciated that the pressure-side linear region of the characteristic curve is phase-displaced with respect to the suction-side linear region of the characteristic curve.

In a peristaltic pump, the rollers of the impeller engage at certain phase angles and disengage at other phase angles. At least one roller is in engagement at any one time, and at no time is the pump "open". Theoretically, a roller pump therefore has no slip, i.e. no deviation between rotation angle and delivered quantity.

When a roller newly engages, the volume of the hose inserted into the pump decreases; when a roller disengages, the volume increases again. Consequently, the pump output, i.e. the volume delivered per rotation angle, is not constant. The pump "pulsates". This pulsation occurs both on the suction side and on the pressure side of the pump.

This non-linear characteristic curve both on the pressure side and on the suction side of the peristaltic pump is disadvantageous for the metering precision, which is particularly disadvantageous if a single peristaltic pump is intended to meter main constituents in quite large quantity and also micro-quantities.

According to the invention, metering from at least one source container is effected by bringing the peristaltic pump to a position such that the metering from this source container takes place entirely in a region with a linear characteristic curve.

The invention is based on the recognition that the metering of micro-quantities is also possible with great precision using a peristaltic pump if, during the whole metering step, the peristaltic pump is moved exclusively in the region with a linear characteristic curve.

It will be appreciated that for this purpose the quantity of the liquid to be metered in this metering step has to be low, such that the entirety of the liquid to be metered can be delivered in an angle region of the impeller of the peristaltic pump, since this does not leave the linear region.

To be able to establish the angle at which an impeller of the peristaltic pump stands, the peristaltic pump preferably comprises a rotation angle encoder.

The peristaltic pump is preferably brought to a position in which the suction-side characteristic curve of the peristaltic pump is linear. In the metering of micro-quantities, the quantity of liquid removed from the source container is especially important, and therefore the linear region of the peristaltic pump present on the suction side is used in order to meter the removed quantity as exactly as possible.

In order to bring the peristaltic pumps to the desired position, i.e. the region with a linear characteristic curve, liquid can be removed from another source container than the one from which metering is intended to take place. In particular, in order to move the impeller, for example to the start of the suction-side linear region, the source container used can be a source container with the above-described universal liquid (UI). While the pump works in the non-linear region, medium is thus removed from the source container with universal liquid.

A very small quantity with a volume of under 10 ml, preferably under 5 ml, particularly preferably less than or equal to 3 ml, is preferably delivered in the region of the linear characteristic curve during a metering step. It will be appreciated that the peristaltic pump has to be dimensioned such that the entirety of the aforementioned volume can be delivered in the region of the linear characteristic curve.

If the volume that can be delivered during a single metering step in the linear region is insufficient, provision is also made, according to one embodiment of the invention, to remove liquid from a source container in several metering steps, and, between these individual metering steps, the peristaltic pump is in each case driven to the start of a linear region.

In the metering steps in which the main constituents of the medical preparation are transferred and in which the metering precision plays a lesser role, the peristaltic pump can be operated conventionally, i.e. both the non-linear region and the linear region of the suction-side and/or pressure-side characteristic curve of the peristaltic pump are traveled through during the respective metering step.

In particular, in at least one further metering step, a quantity with a volume of over 15 ml, preferably over 20 ml, is delivered, wherein the peristaltic pump is operated both in the region with a linear characteristic curve and also in a region with a non-linear characteristic curve. The main constituents of the medical preparation are preferably metered in this way.

By virtue of the invention, it is possible in particular that all of the metering steps during the production of the medical preparation are carried out with great precision by means of a single peristaltic pump.

In a development of the invention, taking the quantity of liquid that is to be removed from the respective source container, the rotation of the impeller required for this purpose is calculated on the basis of the suction-side characteristic curve of the peristaltic pump.

In each metering step, the quantity of liquid removed from the respective source container can be determined via the rotation of the peristaltic pump, in particular via the angle and the number of revolutions of an impeller of the peristaltic pump. On the basis of the predefined quantity of liquid to be removed, the pump is thus activated and the necessary rotation angle for a metering step is calculated.

The metering, hence the activation of the peristaltic pump at each metering step, is not therefore based on a constant delivery rate. Instead, the suction-side fluctuation of the pump output is allowed for on the basis of a previously determined and stored characteristic curve.

This also improves the metering precision in metering steps in which the peristaltic pump is not operated exclusively in the linear region.

At or after each metering step, the target container is preferably weighed and the quantity of the respectively transferred liquid is thus checked.

However, this check on the basis of the weight of the target container is preferably not carried out based on the calculated quantity on the basis of the suction-side characteristic curve of the peristaltic pump, and instead the pressure-side characteristic curve of the peristaltic pump is taken into consideration in calculating which quantity of liquid was transferred into the target container upon rotation of the impeller by the previously calculated rotation angle.

If this calculated quantity of liquid transferred into the target container agrees with the result of the weighing of the target container, the respective metering step can be regarded as correct. By contrast, if the results do not tally or they lie outside a predefined tolerance range, an error can be indicated on the installation, for example on a display.

Depending on the nature and importance of the difference between the calculated quantity and the weighed quantity, the person using the installation may be prompted, for example by indications on a display, to discard the target container and fill a new target container and/or calibrate the installation.

Particularly when micro-quantities are being metered, it can happen that, after removal of a predefined quantity of liquid from a source container, the liquid does not arrive directly in the target container, and instead it is initially located in the transfer set, for example in the hose inserted into the peristaltic pump. The liquid which is located in the transfer set in front of this liquid, and which is now pressed into the target container, can have another density. Therefore, the weight increase of the target container is not on its own a sufficiently precise measure of the transferred quantity.

In one embodiment of the invention, the quantity of the liquid delivered by the peristaltic pump is calculated. When weighing the target container, account is taken of the sequence and quantity of different liquids in the inflow of the target container, in order to allow for the density of the liquids in the check during weighing.

This embodiment of the invention is based on the recognition that the precision of the check carried out in each metering step is increased by taking into consideration the density, i.e. the specific weight, of the respective liquid transferred into the target container.

In this calculation, the inflow of the target container is divided theoretically into sections, in each of which a liquid with a different density is located.

Preferably taking into consideration the pressure-side characteristic curve of the peristaltic pump, it is now possible to predict which liquid or liquids are introduced into the target container during a metering step.

This principle is based on the understanding that all of the liquids removed from the source containers ultimately arrive in the target container. Since the volume of the section from the source container or from the valve, starting from which the liquid of the respective source container flows into the valve unit, to the source container located on the balance is known, it is possible to calculate which liquid or which liquids arrives or arrive in the target container in one metering step.

The volume is determined by the valve unit, starting from the position of the respective valve of the source container, and also by the hose guided through the peristaltic pump and connecting the valve unit to the target container.

The check of the respective metering step by weighing the target container is therefore not based on the density of the liquid removed in the respective metering step, but instead on the density of the liquid or liquids introduced into the target container. On account of the volume of the inflow and of the peristaltic pump, the density of the introduced liquid may differ at least at the start of the metering step.

It will be appreciated that the liquids arranged in an inflow and/or in a hose of the peristaltic pump are not separated from each other exactly according to this calculation model, and instead different liquids mix in the region of the interface. However, it has been shown that these mixing effects can generally or approximately be ignored.

In one embodiment of the invention, the target container is weighed at each individual metering step, and the quantity of the liquid transferred into the target container is thus checked at each individual metering step.

A check of each individual metering step is preferably also permitted in the case of micro-quantities by virtue of the fact that the quantity of the liquid transferred into the target container at one metering step is calculated taking into consideration the pressure-side characteristic curve of the peristaltic pump.

In conventional installations for the preparation of parenteral nutrition, a precision weighing cell can be used at the end of the filling procedure, i.e. after completion of all the metering steps, to check whether the weight increase of the target container tallies with the desired quantity of the individual constituents that is to be metered.

At least with micro-quantities, however, a sufficiently precise assessment of each individual metering step is in principle not possible on account of the non-linear characteristic curve on the pressure side.

By contrast, by taking account of the pressure-side characteristic curve and/or by operating the peristaltic pump in the linear region during the metering of micro-quantities, a check of the individual metering step can be carried out by weighing the target container, in particular also in micro-quantities.

This increases the certainty that the composition of the medical preparation corresponds to the requirements.

In the metering of micro-quantities, occlusions can additionally occur that are difficult to detect at the installation. For example, if the hose leading from a source container to the peristaltic pump is blocked, the peristaltic pump, in the case of a small quantity, in particular a quantity of under 3 ml, still delivers liquid into the target container, since the flexible hoses of the transfer set can contract. If the valve to another source container is now subsequently opened, the hose relaxes by suctioning liquid out of the other source container.

Under certain circumstances, this effect can have the consequence that the total quantity checked by weighing the target container is the same at the end of all the metering steps, but an individual micro-quantity is present in completely false metering or not at all.

Therefore, in a development of the invention, the delivery rate of the peristaltic pump is checked by means of a flow sensor. The flow sensor is preferably arranged on the suction side. A flow sensor can in particular be provided in which a hose of the transfer set is inserted.

Such flow sensors are known. It has been found, however, that they are not suitable for exactly determining the throughflow quantity even at a very low flow velocity.

In the case of a blockage, or in the event of a valve of the transfer set not opening, the flow sensor can however be used to establish such a great deviation from a desired value that it can be inferred therefrom that the throughflow quantity at the current theoretical delivery rate of the pump is not plausible.

The method can then be discontinued, and the person using the installation can be informed via an error message.

In a development of the invention, a bubble sensor (bubble detector) is used in order to check, in an inflow to the target container, that no bubbles are delivered in the hose.

This bubble sensor, which can be configured as an ultrasonic sensor for example, is preferably located on the pressure side with respect to the peristaltic pump. It is in particular a sensor into which the hose of a transfer set can be inserted.

If bubbles are present above a threshold value, the method can likewise be stopped and the user can be informed by means of an error message.

In a preferred embodiment of the invention, the metering factor of the peristaltic pump is determined in a preceding calibration step by means of weighing a target container.

The metering factor is the volume which is delivered during delivery of a defined liquid, in particular during delivery of water, at a defined speed of the impeller and a full revolution of the pump. The metering factor depends, among other things, on tolerances of the hose inserted into the pump. When the installation is put into operation, this metering factor can be calibrated when filling a target container in order to adapt the activation of the peristaltic pump to a newly used transfer set.

Provision is made in particular that, when putting into operation the installation for producing the medical preparation, a first target container is used which is subsequently discarded, this being referred to as a waste bag. This waste bag (waste container) is attached by means of the transfer set, and the hoses leading to all of the source containers are vented, by in each case removal of a required quantity of liquid.

In order to determine the metering factor, liquid, preferably water, can be delivered into the waste bag and the metering factor can be determined in the process. After the waste bag has been discarded, this metering factor is used as a basis for calculating the quantity delivered by the pump in further metering steps.

It will be appreciated that the metering factor is in turn correlated with the above-described consideration of the non-linear region of the suction-side and pressure-side characteristic curve of the peristaltic pump.

Moreover, the pump output of a peristaltic pump also depends, among other things, on the medium that is to be delivered, in particular on the viscosity of the liquid that is to be delivered. This dependency can likewise be taken into consideration in the calculation of the delivered quantities, as is provided for in one embodiment of the invention.

A flow factor of 1.0 can be set for water. For other media, for example glucose, this flow factor assumes higher values, for example values of up to 1.1. This can be taken into consideration in the calculation of the delivered quantities, in particular of the delivered quantities of main constituents, by including the flow factor in the calculation of the delivered volume.

In a development of the invention, the metering factor of the peristaltic pump is calibrated, preferably with UI, during the production of the medical preparation when an impeller of the peristaltic pump rotates through at least one full revolution.

Thus, the metering factor of the peristaltic pump is not just determined initially when the installation is put into operation. Instead, the metering factor is also checked, and optionally recalibrated, if possible during the regular operating of the installation, i.e. during the production of medical preparations.

Provision is made in particular that, in addition to an initial calibration by determination of the metering factor, there are several further determinations, preferably at least three further determinations, of the metering factor during the period of use of a transfer set.

This calibration during ongoing operation is preferably carried out when a sufficient quantity of universal liquid or water is transferred into the target container, since the flow factor of this universal liquid is always 1.0, such that no error arises in the calibration on account of a different flow factor. The calibration during ongoing operation preferably takes place during delivery of the same liquid as was used for the initial determination of the metering factor using the waste bag.

Particularly preferably, the calibration during ongoing operation is carried out only when the transfer set is flushed with universal liquid, and the inflow of the target container thus has no sections in which another liquid is located.

Therefore, since only liquid with the same density and the same viscosity is delivered during the entire calibration, a greater precision of the calibration is achieved.

The above-described method steps according to the invention can be implemented by devices that are accordingly designed or suitable for executing the described method steps. These devices can be a constituent part of a system.

The scope of the invention therefore also includes an installation for producing a medical preparation, in particular an installation for producing parenteral nutrition, comprising a peristaltic pump and a system for carrying out a method as per the above-described invention.

The method according to the invention can be carried out in particular by means of the installation according to the invention. The installation with the system according to the invention is in particular configured to carry out the method according to the invention.

BRIEF DESCRIPTION OF THE DRAWINGS

The subject matter of the invention is explained below on the basis of an illustrative embodiment and with reference to FIG. 1 to FIG. 11 in the drawings.

DETAILED DESCRIPTION OF THE DRAWINGS

Figure 1:
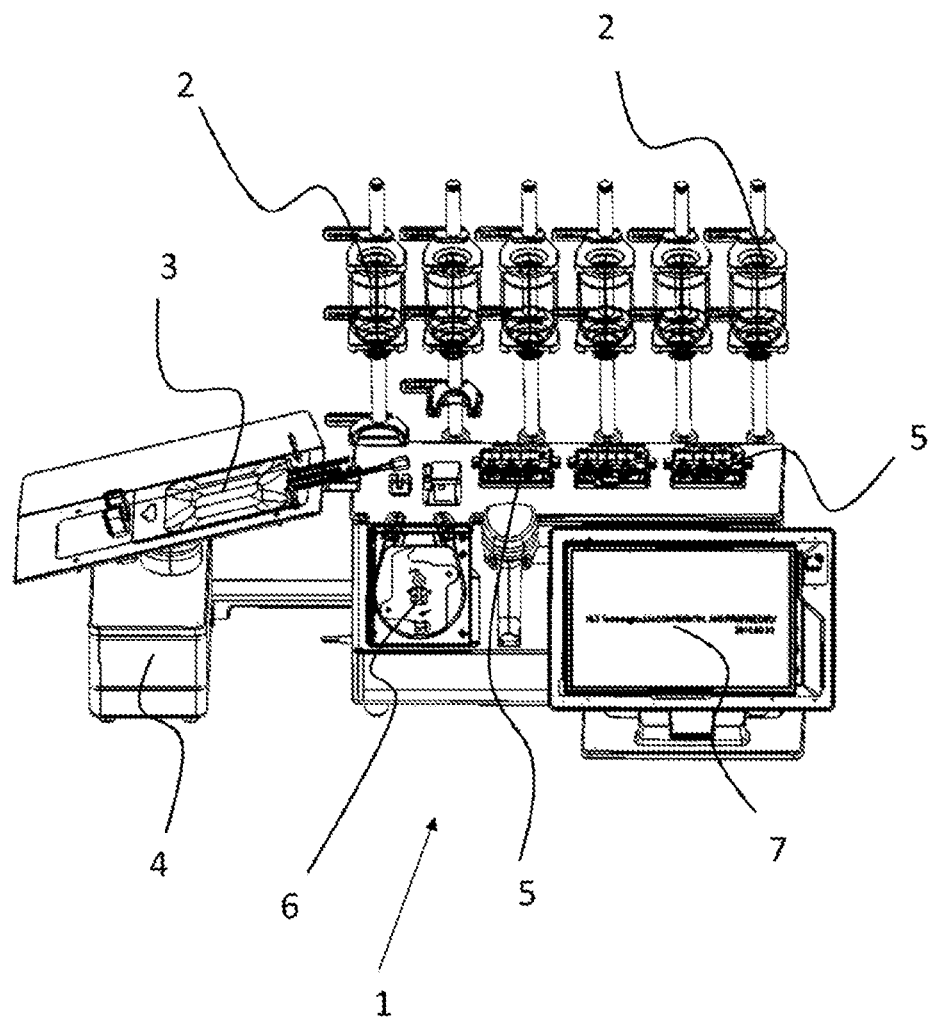
FIG. 1 shows a perspective view of an installation for producing a medical preparation, as is used for the method according to the invention.

FIG. 1 shows an installation 1 for producing a medical preparation.

The installation 1 for producing a medical preparation comprises a multiplicity of source containers 2, of which only some are shown in this view. In particular, this illustration does not show those source containers comprising the main constituents of the medical preparation, nor the container filled with universal liquid. These containers can in particular be suspended at a location remote from the installation, e.g. on a hook secured to a rail.

A target container 3 can be seen which is configured as an infusion bag and is arranged on a balance 4. During the operation of the installation 1, the quantity of the liquid transferred into the target container 3 can be checked via the balance 4.

To put the installation 1 into operation, a transfer set is used which comprises a valve unit 5 and hoses by means of which the valve unit 5 is connected on the one hand to the target container 3 and on the other hand to the source containers 2.

During the production of a medical preparation, one valve of the valve unit 5 is opened in each metering step via the installation 1, such that liquid can be pumped from precisely one source container 2 into the target container 3.

In order to deliver the liquids, the installation 1 here has a single peristaltic pump 6 by means of which liquids can be pumped from all of the source containers 2 into the target container 3.

The installation 1 moreover has a display 7 which is configured as a touch screen, for example, by means of which the user can program the installation 1 and can in particular select a program by means of which a target container 3 is filled with a predefined composition of constituents.

The installation comprises an electronic control (not shown) via which the peristaltic pump 6 is activated and which is connected to the balance 4.

Figure 2:
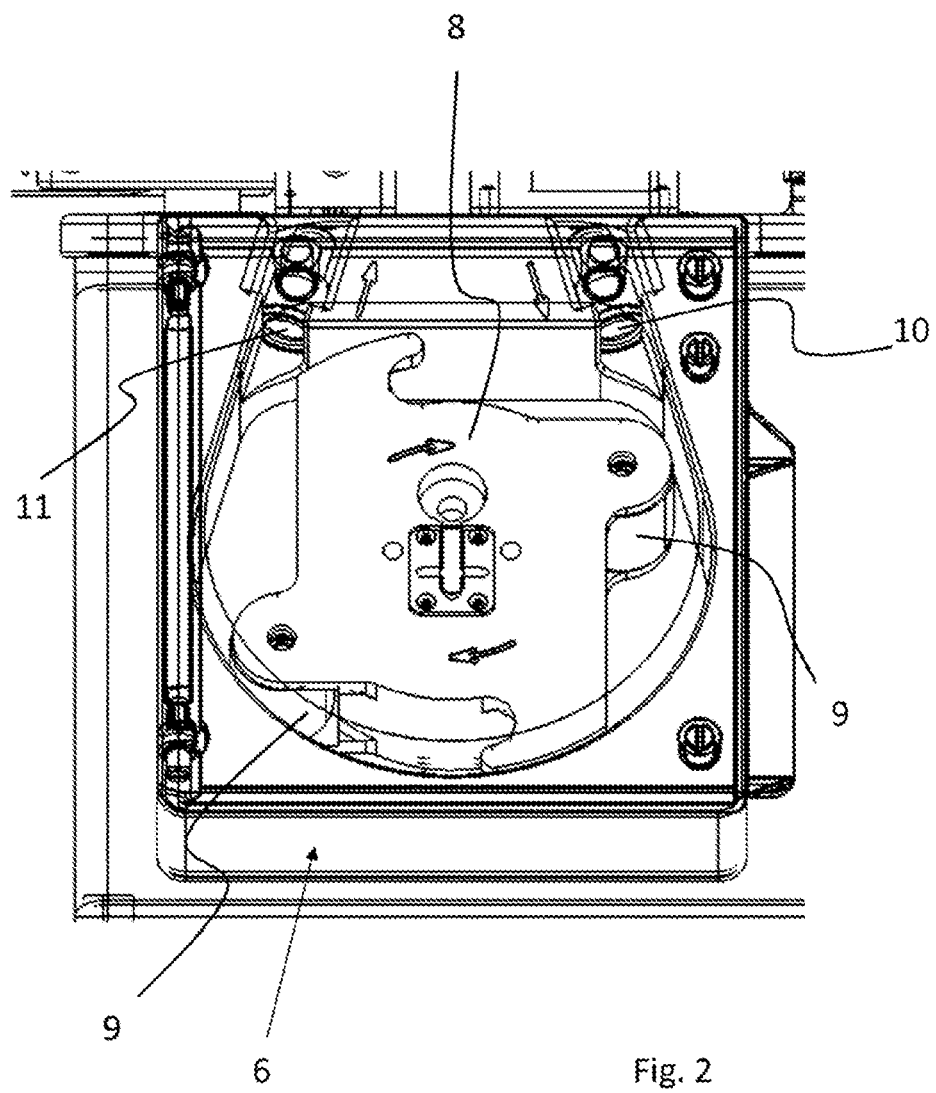
FIG. 2 is a detailed view of the peristaltic pump.

FIG. 2 is a detailed view of the peristaltic pump 6. The latter is preferably provided here as a roller pump.

It will be seen that the peristaltic pump 6 has an impeller 8 with two rollers 9. The hose to be inserted is not shown in this view.

It will be appreciated that the method according to the invention can also be carried out with a peristaltic pump having a different number of rollers, in particular with a peristaltic pump that comprises three rollers (not shown).

When a hose (not shown) is inserted into the peristaltic pump 6, the peristaltic pump has an inlet 10 and an outlet 11. In the position of the impeller 8 shown here, both rollers 9 are in engagement with the hose.

However, it will be appreciated that, when the rollers 9 move from the outlet 11 to the inlet 10, they are in part not in engagement with the hose. This results in a non-linear characteristic curve of the pump output both on the suction side, i.e. on the side of the inlet 10, and also on the pressure side, i.e. on the side of the outlet 11, and the peristaltic pump pulsates.

The quantity of the liquid delivered in one full revolution is preferably between 5 and 50 ml.

In order also to be able to precisely meter micro-quantities, i.e. quantities in the lower milliliter range, the peristaltic pump 6 according to one aspect of the invention is brought to a position, by rotation of the impeller 8, in which the respective micro-quantity can be metered completely in the at least suction-side linear region of the peristaltic pump 6.

For this purpose, the peristaltic pump comprises a rotation angle encoder (not shown).

In the position of the impeller 8 shown here, a roller 9 has just passed the inlet 10 and is now in engagement with the inserted hose.

For the metering of a micro-quantity, it is recommended that the peristaltic pump 6 is brought to the position shown here in order then to be able to meter the micro-quantity completely in the region of the suction-side linear characteristic curve of the peristaltic pump 6.

Figure 3:
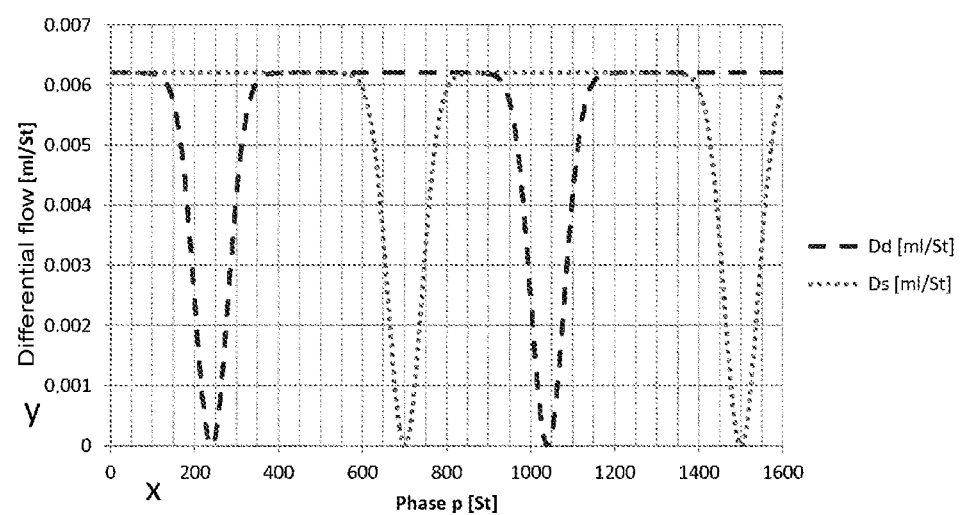
Referring to FIG. 3, the characteristic curve of a peristaltic pump will be explained on the basis of an illustrative embodiment.

FIG. 3 shows the pressure-side and suction-side characteristic curve.

The phase angle p is divided into 1600 units, which are plotted on the x axis. These 1600 steps represent a full revolution of the pump.

The differential flow, i.e. the volume delivered per rotation angle unit, for the peristaltic pump is plotted on the y axis.

The dashed characteristic curve represents the pressure-side differential flow, and the dotted characteristic curve represents the suction-side differential flow.

It will be seen that the characteristic curves are constant over wide regions, i.e. regions with a linear characteristic curve are present.

However, each characteristic curve has two falls. On the suction side, these are the phase angles at which one of the two rollers comes newly into engagement (p=700 and p=1500). In these regions, the volume of the hose of the peristaltic pump decreases in proximity to the suction-side attachment. The suction rate of the pump is reduced.

On the pressure side, the falls are located in those regions where a roller comes out of engagement. The hose of the peristaltic pump then returns to its original shape. The hose increases its volume and the delivery rate of the pump is reduced on the pressure side.

For exact metering, in particular of a micro-quantity, the delivered volume of the suction side is relevant. All the liquid removed from the source container in the respective metering step ultimately arrives at the target container. It is therefore crucial that the correct volume is removed at the suction side in each metering step.

According to the invention, when metering a so-called micro-quantity, liquid is now delivered only in one of the two linear regions of the suction side of the pump in a metering step.

For this purpose, before the start of the metering step, the peristaltic pump is set preferably to the start of the next linear region of the suction side by pumping of universal liquid. In this example, these positions are approximately at p=50 and p=850.

Thus, micro-quantities can also be metered exactly with a single peristaltic pump.

The suction-side characteristic curve of the peristaltic pump is preferably used to permit more exact calculation of the quantity of liquid removed from the source container.

It is thus also possible, in metering steps that take place in the non-linear region of the peristaltic pump, to use the suction-side characteristic curve of the peristaltic pump in order to calculate the quantities of the liquid removed.

It is thus taken into account, in the calculation, that the suction-side delivery rate of the peristaltic pump is not linear.

Taking the characteristic curve Ds, the phase angle p2 is determined such that $Vs = \int_{p1}^{p2} Ds(p) dp$ gives the volume to be metered. Here, p1 is the position of the impeller at the start of the metering step, and p2 is the position after the metering step. The variable Vs is the volume to be removed from the source container.

The pressure-side characteristic curve of the pump can in turn be used to check, in an improved manner by weighing the target container, whether the quantity actually removed corresponds to the calculated quantity.

For this purpose, the volume of the liquid arriving in the target container is calculated. Moreover, based on the known density of the delivered liquid, the mass of the incoming liquid is calculated. The characteristic curve Dd of the pressure side is used to determine the volume of the liquid arriving in the target container.

The characteristic curves, preferably determined by empirical measurements, can be stored, for example, as approximate formulae or also as at simple value table in order to calculate the suction-side and pressure-side pump output as a function of the phase angle. In particular, the characteristic curves can be determined by measurement and then approximated by an empirical formula. The calculations in the installation then take place by means of the empirical formula or via a value table.

Figure 4A:
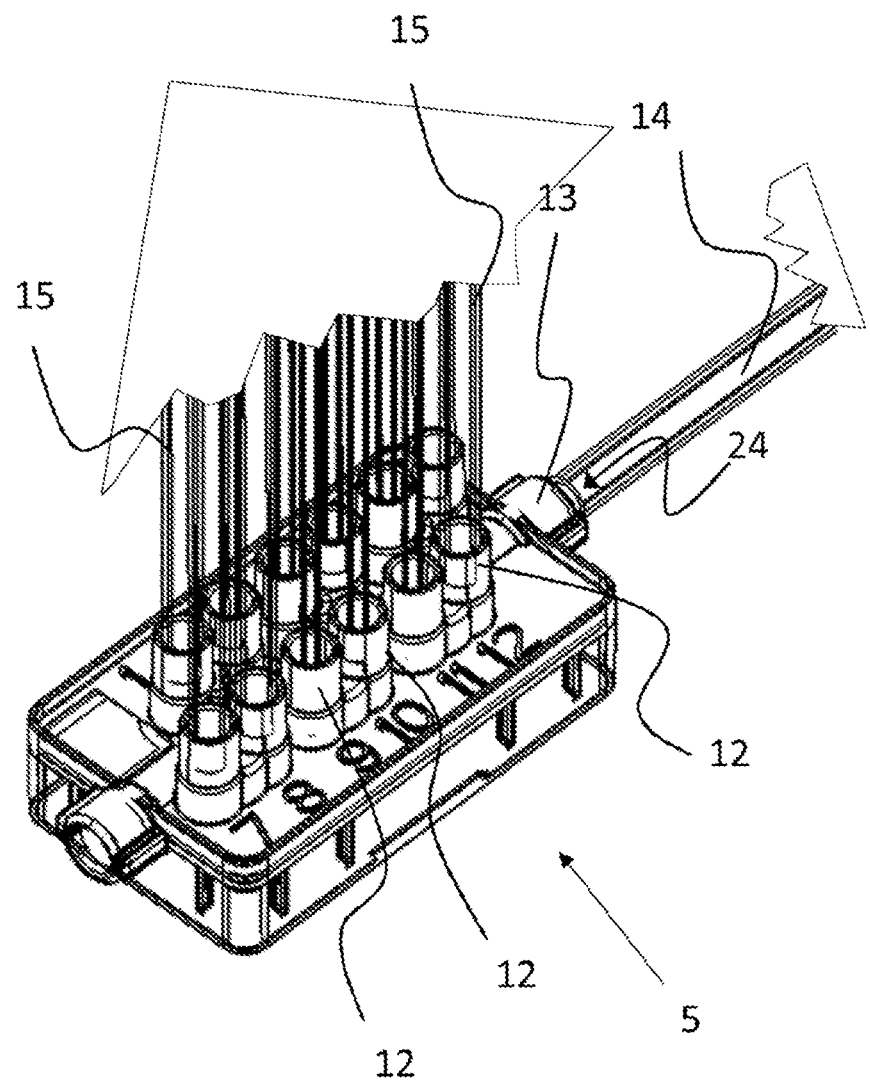
FIGS. 4a to 4c are detailed views of the valve unit of the installation for producing a medical preparation, along with the hoses of said valve unit.

FIG. 4a is a perspective view of the valve unit 5 used for the installation for producing a medical preparation.

The valve unit 5 comprises a multiplicity of inflows 12, which are connected by hoses 15 to the source containers (2 in FIG. 1). By way of valves (not shown) integrated in the valve unit 5, a hose 15, by means of which liquid is removed from a source container, can be connected selectively to a hose 14, which is arranged at the outflow 13 of the valve unit 5.

The hose 14 moreover has a portion which is placed into the peristaltic pump.

Figure 4B:
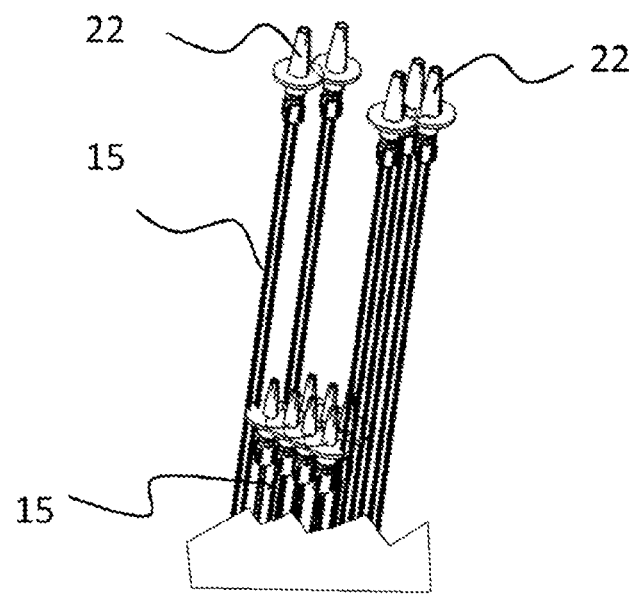

FIG. 4b shows the ends of the hoses 15 for attachment of the source containers. The attachments 22 for the source containers can be seen, which attachments are configured in this illustrative embodiment as Luer lock attachments with an attached spike.

Figure 4C:
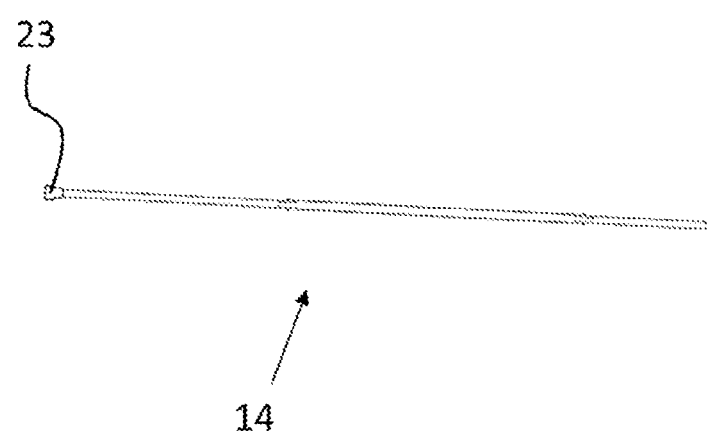

FIG. 4c shows the hose 14 which forms the outflow of the valve unit 5 and at the same time the inflow of the target container. The attachment 23 for the target container can be seen.

The valve unit 5 shown here forms, together with the hoses 14, 15 and the attachments 22, 23 thereof, the transfer set that is used for operating the installation.

This transfer set is preferably designed as a disposable item and is regularly replaced. By virtue of this design, the liquids to be transferred come into contact only with components of the transfer set on their way from the source container to the target container.

Figure 5A:
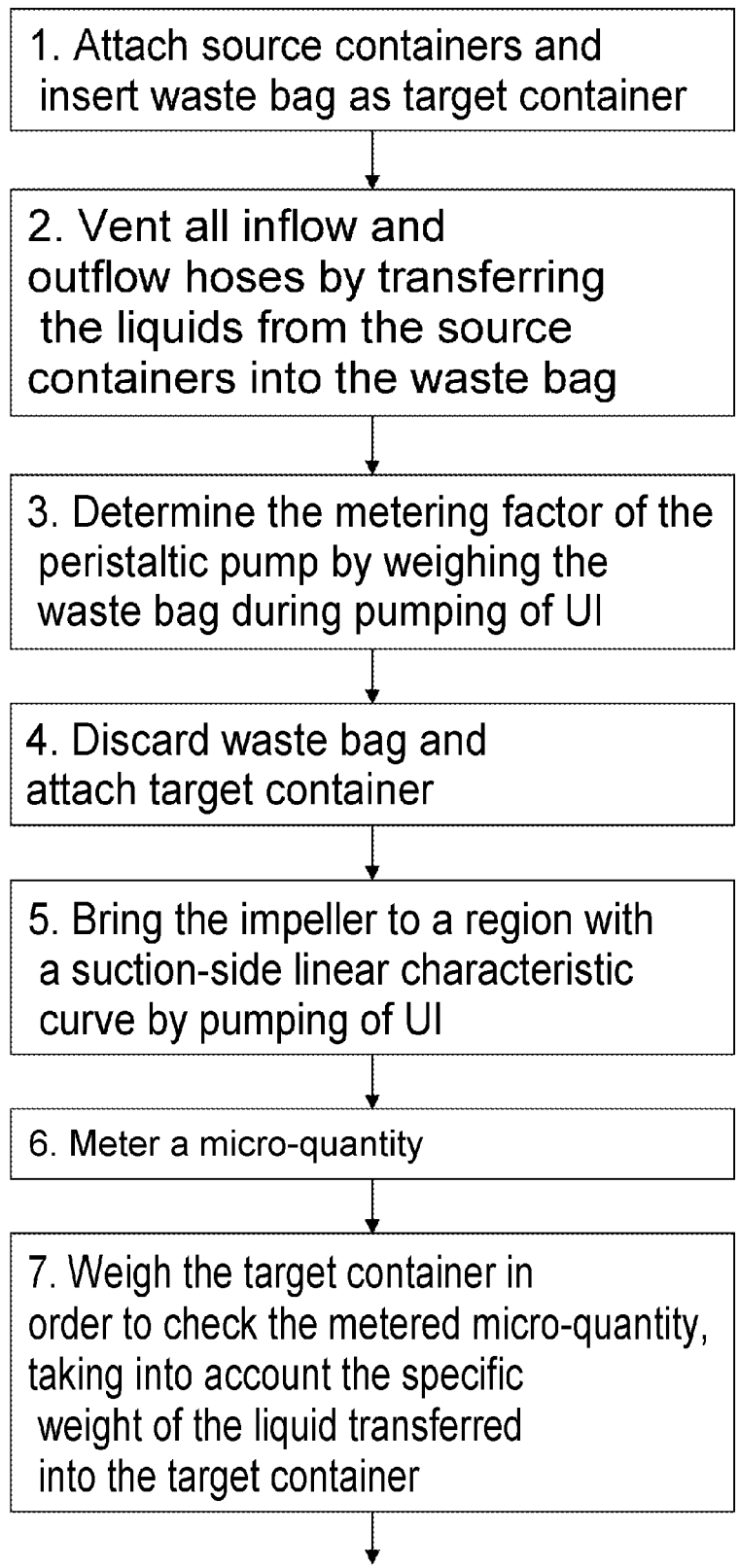
FIG. 5a and FIG. 5b each show, in a flow chart, the method steps in an illustrative embodiment of the method according to the invention.
Figure 5B:
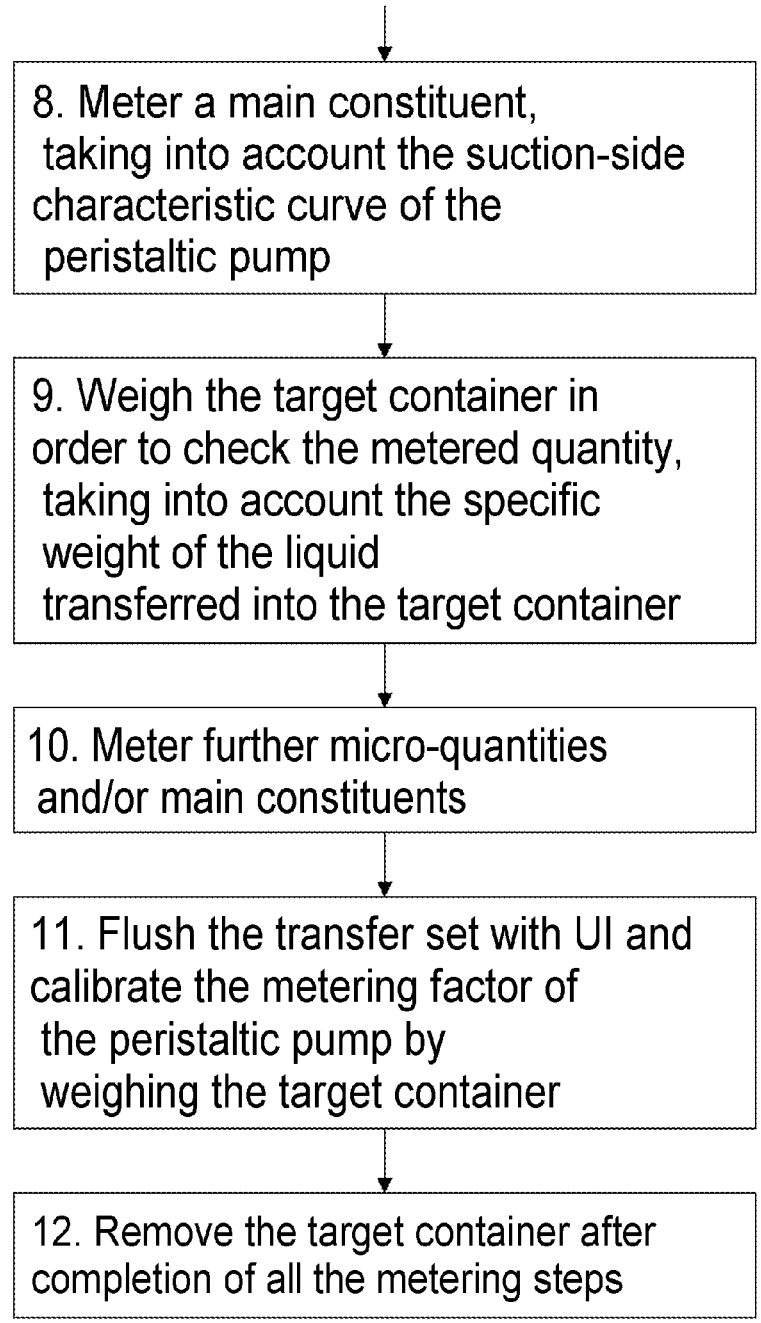

An illustrative embodiment of a method according to the invention for producing a medical preparation will be explained with reference to the flow chart in FIG. 5a and FIG. 5b.

First, the above-described transfer set is used to attach the source containers. Moreover, a container known as a waste bag is inserted as target container, i.e. a container which is not intended to be used for applying a medical preparation but is instead discarded after the installation has been prepared.

The whole transfer set including the hoses is filled with universal liquid (UI), for example isotonic water, and each valve is opened until the hoses (15 in FIGS. 4a and 4b) leading to the source containers are filled and free of bubbles.

The metering factor of the peristaltic pump can then be determined by weighing the waste bag during the pumping of universal liquid. The pump output of the peristaltic pump, which changes particularly on account of tolerances of the used hose, is now calibrated by determination of this metering factor.

The waste bag is then discarded, and the first target container that is to be filled with a medical preparation can be attached.

In this illustrative embodiment, a micro-quantity is first of all intended to be metered in a first metering step.

Therefore, in step 5, the impeller is brought to a region with a suction-side linear characteristic curve, with universal liquid initially being delivered during the movement of the impeller to this position.

A micro-quantity can now be removed from the source container completely in the suction-side linear region of the characteristic curve of the pump.

Each individual metering step, i.e. also the step for metering a micro-quantity, is checked by weighing the target container.

The density of the liquid transferred into the target container is taken into consideration here by calculating which liquid or which liquids are located in the inflow of the target container and are transferred into same during the removal of the micro-quantity in step 5.

Moreover, during the check made by weighing, a calculation is also made, taking into consideration the pressure-side characteristic curve of the peristaltic pump, to establish as exactly as possible which volume was transferred into the target container in the respective metering step. On account of the phase-displaced characteristic curves of suction side and pressure side, this volume does not always tally.

A main constituent of the medical preparation is then metered, taking into consideration the suction-side characteristic curve of the peristaltic pump. In contrast to the metering of micro-quantities, the peristaltic pump is also operated in the non-linear region in the metering of the main constituents.

However, in the calculation of the quantity of the respective main constituent removed from the source container, the suction-side characteristic curve of the peristaltic pump is taken into account in order to be able to accurately predict the volume removed on the suction side.

The checking of the quantity removed from the source container for a main constituent is also carried out taking into consideration the density of the liquid transferred into the target container and taking into consideration the pressure-side characteristic curve of the peristaltic pump.

In the metering of micro-quantities and also in the metering of main constituents, a further factor included in the calculation of the volume of the delivered liquid is preferably also a flow factor, which is dependent on the nature, in particular the viscosity, of the delivered liquid. Water is assigned a flow factor of 1.0; the flow factor changes considerably in the case of viscous components such as glucose solutions.

It has been found sufficient to take into account a generalized flow factor as a function of the liquid removed in each metering step, since a viscosity-induced effect on the pump output is present in the first place on account of the constriction (e.g. spike) present at the attachment of the source container.

The weight added to the target container in a metering step can be calculated in detail as follows:

$$F*Vs = \int_{p_1}^{p_2} Ds(p)dp$$

Vs is the volume to be metered in a metering step. This volume corresponds to the volume of the suction side at which a source container is attached.

p1 is the position of the impeller before the metering step, in particular the end position of a previous metering step or the start of the linear region into which the impeller was previously rotated.

p2 is the calculated position of the impeller after the metering step, i.e. the result of the calculation for the rotation angle of the pump in the metering step.

F is the flow factor, i.e. the correction factor for the respective viscosity of the medium.

Ds(p) is the characteristic curve of the suction side (constant) and p is the phase of the impeller.

The phases p1 and p2 can here differ by several revolutions.

The flow factor F is therefore a correction for an additional slip of the pump by a viscosity greater than that of water. The volume to be metered is in particular higher than that of water by the factor F.

Almost all media used for a medical preparation have the same viscosity as water or a higher viscosity than water. Media with a lower viscosity are very rare. Generally, therefore, F≥1.

The volume which is expected on the pressure side, and on the basis of which the weight of the liquid quantity delivered to the target container in a metering step is calculated, measures:

$$Vd=\int_{p_1}^{p_2} Dd(p)dp$$

This calculated weight serves for checking the respective metering step via the balance.

Vd is the volume expected on the pressure side, i.e. the volume of liquid which is delivered, in the metering step, into the target container located on the balance.

Dd(p) is the characteristic curve of the pressure side. The flow factor F is not included in the calculation of the volume delivered on the pressure side, since the "slip" of the pump is of course not delivered The expected mass increase G on the balance is then:

$$G=Vd*\rho,$$

with the density ρ of the delivered medium.

ρ is therefore the specific weight of the liquid transferred into the target container in a metering step, i.e. initially of the liquid that is already present in the inflow of the target container. If several different liquids are transferred into the target container during a metering step, the specific weight of the liquids is correlated with their quantity.

In a next step, further micro-quantities or further main constituents are delivered in further metering steps. Steps 5 to 9 can therefore be repeated until all of the desired constituents are in the target container.

It will be appreciated that steps 5 to 7, i.e. the metering of a micro-quantity, and steps 8 and 9, i.e. the metering of a main constituent, are also interchangeable, i.e. can be carried out in a different sequence.

At the end of each filling procedure, the transfer set is flushed with universal liquid and, if appropriate, the desired residual quantity of universal liquid is fed to the target container.

It is proposed that this flushing phase for example, in which the impeller of the peristaltic pump rotates by more than one complete revolution, is utilized in order to newly determine the metering factor of the peristaltic pump during ongoing operation, by means of the target container being weighed. The metering factor can thus be recalibrated during ongoing operation. This factor may change, for example on account of the elasticity and shape of the hose inserted into the peristaltic pump changing.

After all of the metering steps have been concluded and the transfer set has been flushed, the target container can be removed and a new target container attached.

It will be appreciated that all of the steps shown here preferably proceed in an automated manner, except for the attachment of the source containers and target container and the start-up of the installation.

Figure 6:
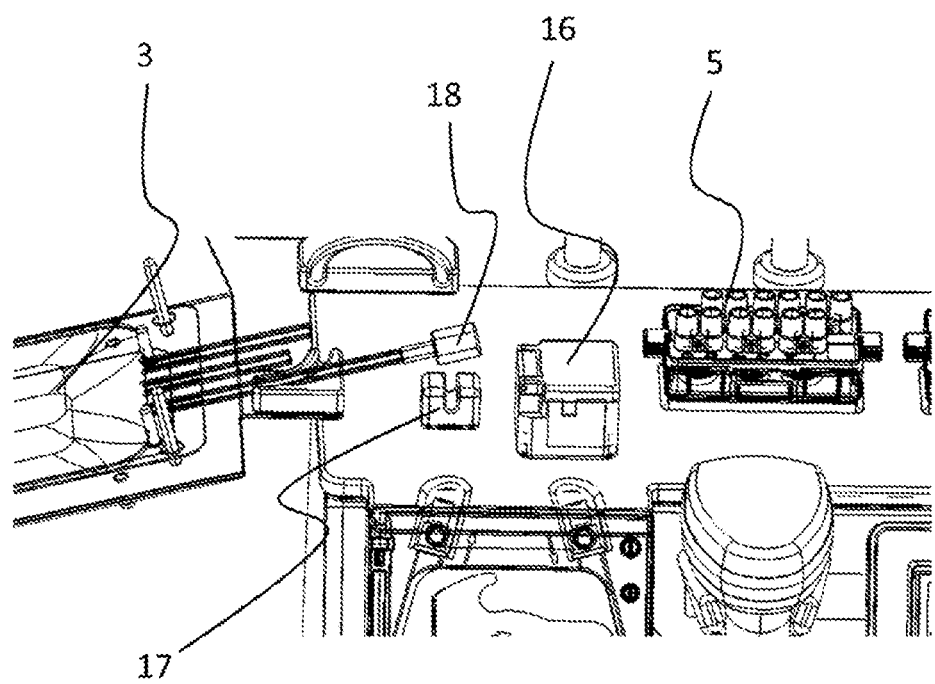
FIG. 6 is a detailed view of the installation for producing a medical preparation, in which flow sensor and bubble sensor can be seen.

FIG. 6 is a further detailed view of FIG. 1. It again shows the target container 3. A valve unit 5 can also be seen.

The hose (not shown here) which connects the valve unit 5 to the target container 3, and which in particular is inserted into the peristaltic pump, is initially inserted into a flow sensor 16.

The suction-side throughflow in the hose is measured via the flow sensor 16, and the delivery rate of the peristaltic pump can thus be checked for plausibility.

If a blockage occurs for example in the region of the valve unit or at the attachment of a source container, the suction-side throughflow will decrease in such a way that an error can be detected by means of the flow sensor 16. Particularly when metering a micro-quantity, the hose will also contract initially in the region of the flow sensor 16, the result of which is that the detected throughflow can be reduced and a blockage can be inferred. An error message can then be generated via the electronic control and indicated to the user.

The flow sensor 16 is preferably designed as an ultrasonic sensor. Particularly at low flow velocities, such a sensor is generally not accurate enough to allow the quantity of the liquid delivered on the suction side to be determined sufficiently precisely via the flow sensor alone.

Therefore, the flow sensor is preferably used alone for monitoring in such a way that an error is assumed when a threshold value is exceeded as regards the difference between the calculated delivery rate of the peristaltic pump, and the resulting calculated throughflow rate, compared to the throughflow rate determined by the flow sensor.

On the pressure side, the hose is inserted into a bubble sensor 17. The latter is an ultrasonic sensor which detects bubbles and, starting from a certain threshold value, switches the installation off and indicates an error to the user.

Figure 7:
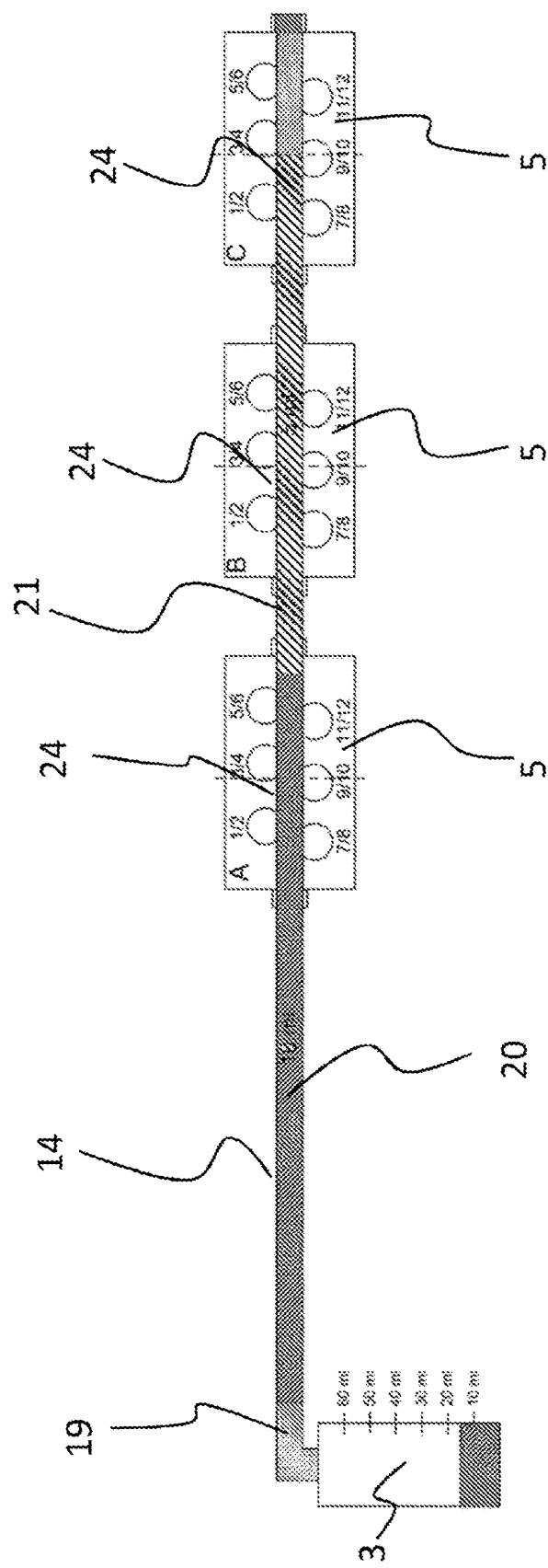
FIG. 7 is a schematic illustration of the inflow of the target container, which illustration will be used to explain the calculation of the quantity transferred into the target container.

FIG. 7 is a schematic view of the hose 14 which connects the valve unit 5 to the target container 3. In this illustrative embodiment, three valve units are shown arranged in succession, although this has no effect on the basic principle. The three valve units 5 shown here can equally well be combined to form a single valve unit.

By means of the valve unit 5, the inflow to a source container is opened in each metering step, such that liquid from the source container can pass through the respective valve of the valve unit, initially into the valve unit and then into the hose 14.

The hose 14 and the collecting channels 24 of the valve units 5 form a volume into which the liquid removed from the respective source containers is initially transferred.

Therefore, the weight of the liquid arriving in the target container 3 in a metering step is not calculated on the basis of the density of the liquid removed in the respective metering step. Instead, the hose 14 and the collecting channels 24 of the valve unit(s) 5 are considered in such a way that different liquids, namely a first liquid 19, a second liquid 20 and a third liquid 21, are located in different sections of the hose 14 and/or of the attached collecting channel 24.

If, for example, a micro-quantity is metered, the specific weight of the first liquid 19 is initially taken as a basis.

The accuracy of the check can be improved by virtue of this theoretical "material stack". In particular, it is possible for each individual metering step to be checked and assessed.

Figure 8:
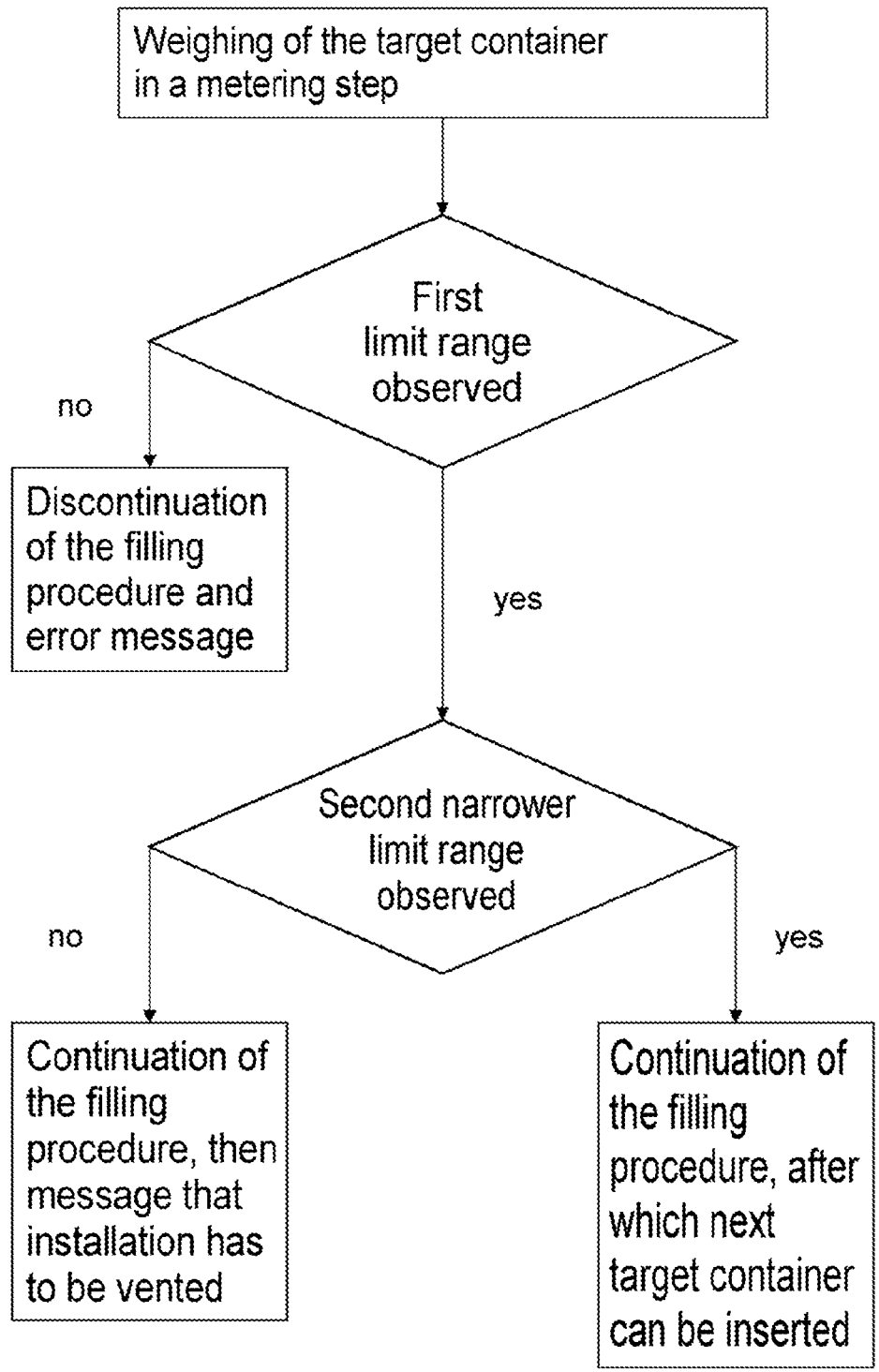
FIG. 8 is a flow chart that will be used to explain how each metering step is checked by weighing the target container.

FIG. 8 is a flow chart that will be used to explain how each metering step is checked by weighing the target container.

In each metering step, the weight transferred into the target container is calculated as a desired weight. This is done, as described above, on the basis of the pressure-side characteristic curve of the peristaltic pump and the specific weight of the liquid transferred into the target container.

If, during the weighing of the target container, the weight determined by the weighing deviates from the calculated weight in such a way as to breach a first limit range that would impair the quality of the medical preparation or that points to an error, the filling procedure is discontinued and an error message is output. If appropriate, the user can then rectify the error, insert a waste bag and recalibrate the installation.

Otherwise, the filling procedure is continued.

If the weight determined by means of the weighing does not lie within a second narrower limit range, which for example points to an insufficient calibration of the installation but points to such a slight deviation of the metered quantity that it does not impair the quality of the medical preparation, then the filling procedure is continued.

However, after completion of the filling procedure, the user of the installation receives a message that the installation has to be calibrated.

Otherwise, the next target container can be inserted after completion of the filling procedure.

Figure 9:
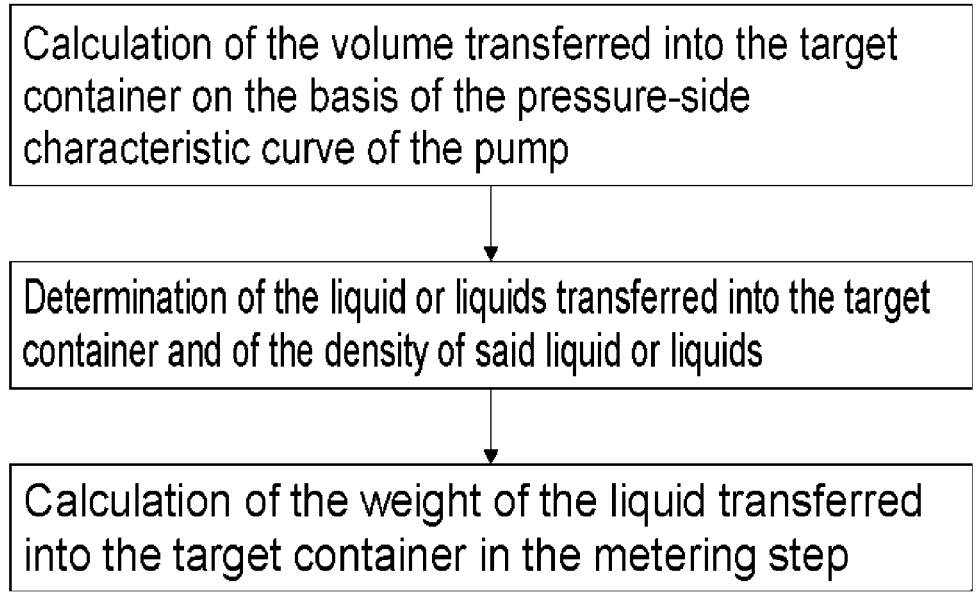
FIG. 9 is a flow chart that will be used to explain how the weight of the liquid transferred into the target container is calculated.

FIG. 9 is a flow chart that will be used to explain how the desired weight is calculated in a metering step.

The volume of the liquid introduced is calculated on the basis of the pressure-side characteristic curve of the peristaltic pump.

It is then determined which liquid or which liquids has or have arrived in the target container in the metering step. This is done in the manner described with reference to FIG. 7.

The desired weight can then be calculated via the specific weight of the transferred liquid or of the liquids.

This desired weight serves for the determination of the limit values mentioned in FIG. 8. Thus, for example, a first limit range could be defined as a deviation of over 10% and a second limit range could be defined as a deviation of over 5%.

It will be appreciated that the limit ranges may also be varied depending on the liquid removed in a metering step, since there are constituents in which deviations in the quantity are more or less critical for the quality of the medical preparation.

Figure 10:
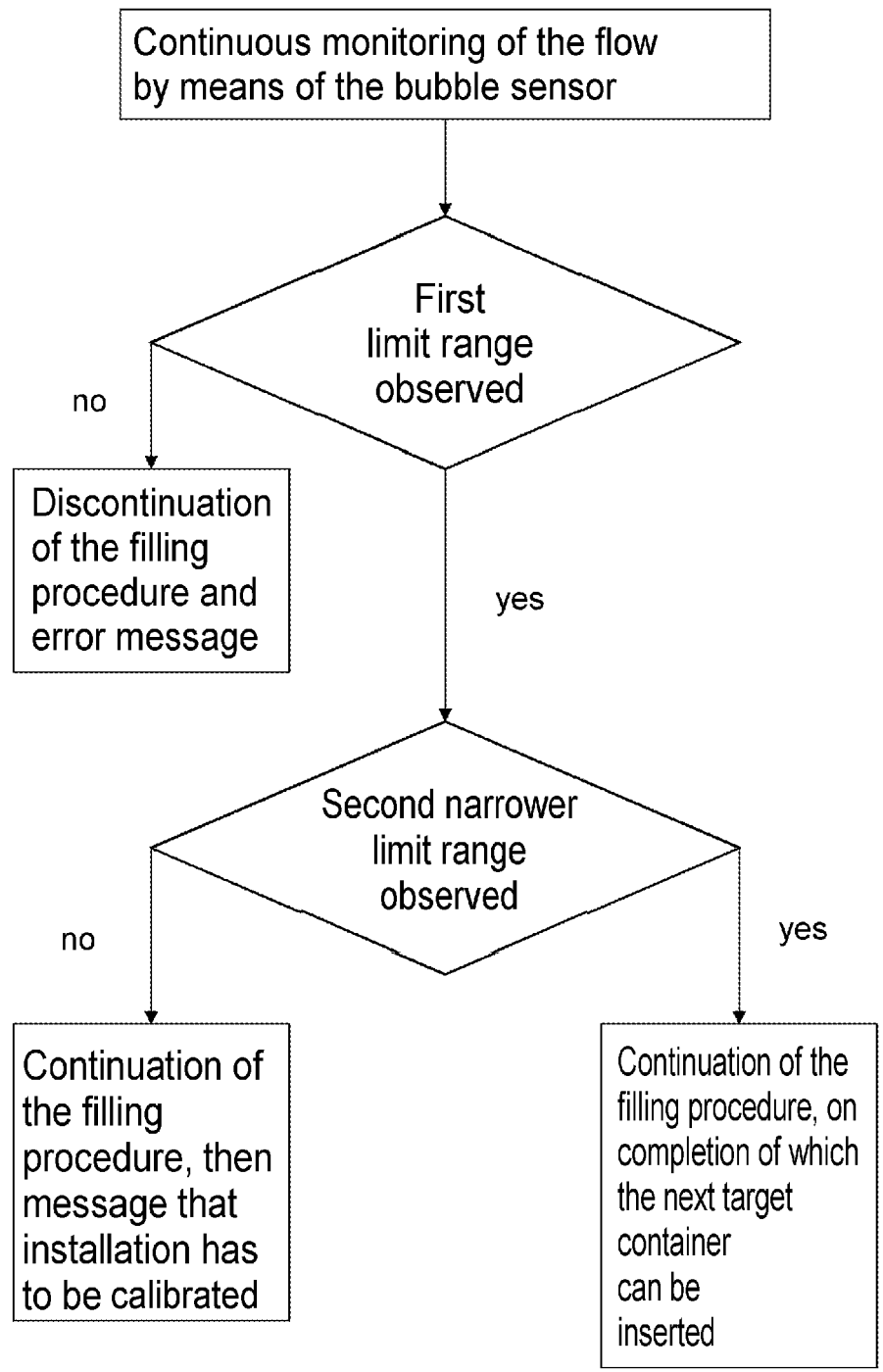
FIG. 10 is a flow chart that will be used to explain the monitoring via the bubble sensor.

FIG. 10 is a flow chart that will be used to explain the monitoring via the bubble sensor.

The quantity of bubbles in the transferred liquid is continuously monitored by the bubble sensor arranged downstream from the peristaltic pump.

In this illustrative embodiment, two limit ranges are also provided.

If the quantity of bubbles is in a limit range that is unacceptable for the quality of the product that is produced, the filling procedure is interrupted and an error message is output.

If a second, narrower limit range is not complied with, the filling procedure can be continued and the target container used as intended, but an error message to the effect that the installation has to be vented is output upon completion of the filling procedure.

Otherwise, the next target container can be inserted after completion of the filling procedure.

Figure 11:
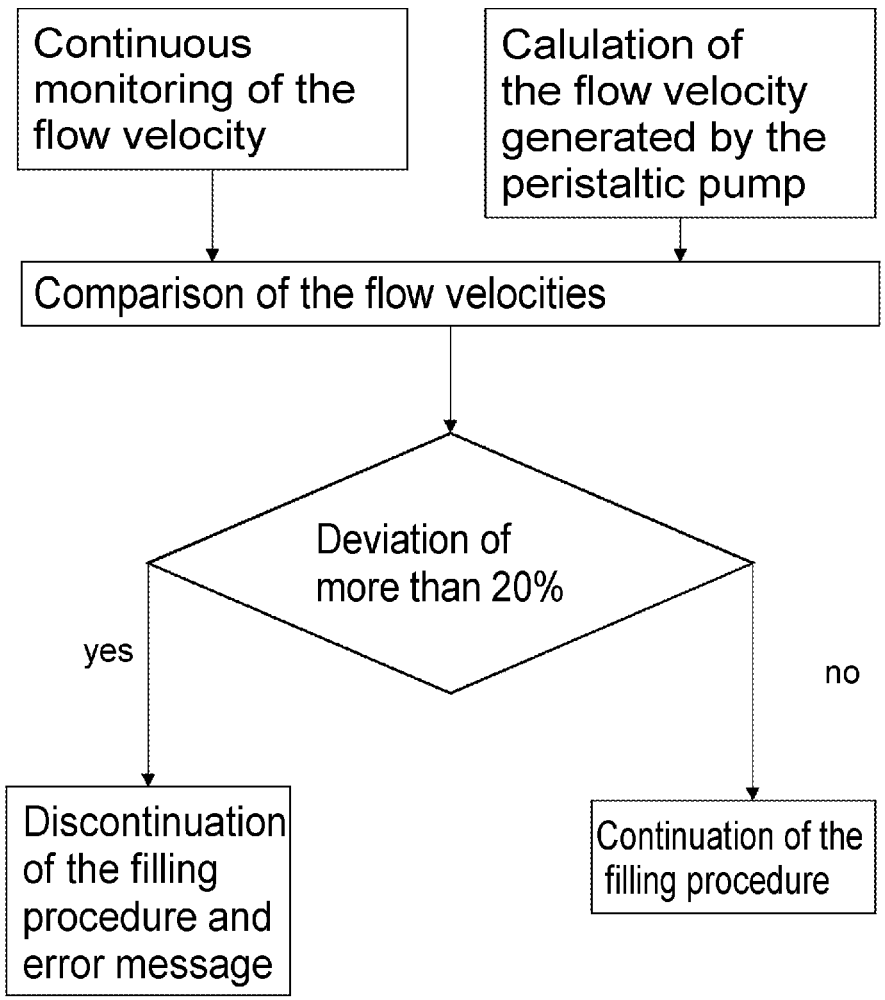
FIG. 11 is a flow chart that will be used to explain the monitoring via the flow sensor.

FIG. 11 is a flow chart intended to explain the monitoring via the flow sensor.

The flow velocity is calculated continuously, preferably on the basis of the suction-side characteristic curve of the peristaltic pump.

In parallel with this, the flow velocity is measured by a flow sensor arranged at the flow side upstream from the peristaltic pump.

Measured flow velocity and calculated flow velocity are compared.

If a deviation is present above a threshold value, in this example 20%, an error (e.g. occlusion) is inferred and the filling procedure is discontinued.

The user is informed via an error message.

To be able to better locate the error, the source container from which liquid was being removed when the error occurred is preferably indicated to the user (e.g. via a number on a screen) for each error message.

By virtue of the invention, the precision in the production of a medical preparation can be improved using a peristaltic pump.

LIST OF REFERENCE SIGNS 1 installation
2 source container
3 target container
4 balance
5 valve unit
6 peristaltic pump
7 display
8 impeller
9 roller
10 inlet
11 outlet
12 inflow
13 outflow
14 hose
15 hose
16 flow sensor
17 bubble sensor
18 attachment
19 first liquid
20 second liquid
21 third liquid
22 attachment
23 attachment
24 collecting channel

The invention claimed is:

1. A method for producing a medical preparation, in particular for parenteral nutrition, the method comprising:
transferring liquids by a peristaltic pump from a plurality of source containers into a target container, wherein the peristaltic pump has at least one region with a linear characteristic curve and one region with a non-linear characteristic curve of the pump output, and metering from at least one source container by bringing the peristaltic pump to a position such that the metering from the at least one source container takes place entirely in the region with the linear characteristic curve of the pump output.

2. The method for producing a medical preparation as claimed in claim 1, wherein the peristaltic pump is brought to a position in which the suction-side characteristic curve of the peristaltic pump is linear.

3. The method for producing a medical preparation as claimed in claim 1, wherein, in order to bring the peristaltic pump to the desired position with a linear characteristic curve, liquid is removed from another source container than the one from which metering is intended to take place, the other source container being from a source container with universal liquid or water.

4. The method for producing a medical preparation as claimed in claim 1, wherein a very small quantity with a volume of under 10 ml is delivered in the region of the linear characteristic curve.

5. The method for producing a medical preparation as claimed in claim 4, wherein the volume is under 5 ml.

6. The method for producing a medical preparation as claimed in claim 1, wherein precisely one single peristaltic pump is used for transferring the liquids from all of the source containers into the target container.

7. The method for producing a medical preparation as claimed in claim 1, wherein, in at least one further metering step, a quantity with a volume of over 15 ml is delivered, wherein the peristaltic pump is operated both in the region with the linear characteristic curve and also in the region with a non-linear characteristic curve.

8. The method for producing a medical preparation as claimed in claim 1, further comprising using an impeller to take a quantity of liquid that is to be removed from the respective source container, wherein a rotation of an impeller required to remove the quantity of liquid is calculated on the basis of the suction-side characteristic curve of the peristaltic pump.

9. The method for producing a medical preparation as claimed in claim 1, wherein at each metering step, the target container is weighed and the quantity of the respectively transferred liquid is thus checked.

10. The method for producing a medical preparation as claimed in claim 1, wherein a quantity of the liquid delivered by the peristaltic pump is calculated and the target container is weighed in order to check the quantity of the liquid delivered, wherein the sequence of different liquids in an inflow of the target container is taken into consideration in order to allow for the specific mass of the liquid in the check during weighing.

11. The method for producing a medical preparation as claimed in claim 1, wherein the target container is weighed at each individual metering step, and a quantity of the liquid transferred into the target container is thus checked at the each individual metering step.

12. The method for producing a medical preparation as claimed in claim 1, wherein a quantity of the liquid transferred into the target container in one metering step is calculated taking into account the pressure-side characteristic curve of the peristaltic pump.

13. The method for producing a medical preparation as claimed in claim 1, wherein a delivery rate of the peristaltic pump is checked with a flow sensor.

14. The method for producing a medical preparation as claimed in claim 1, wherein a metering factor of the peristaltic pump is determined in a preceding calibration step by means of weighing a target container.

15. The method for producing a medical preparation as claimed in claim 1, wherein in order to transfer the liquids from the source containers into the target container, a transfer set is used which comprises a valve unit, a hose, which is insertable into the peristaltic pump, and a plurality of hoses for attachment of the source containers.

16. An installation for producing a medical preparation, in particular an installation for producing parenteral nutrition, comprising a peristaltic pump and a system for carrying out a method as claimed in claim 1.

17. The method for producing a medical preparation as claimed in claim 1, wherein a bubble sensor is used to check that there are no bubbles in an inflow to the target container.

18. The method for producing a medical preparation as claimed in claim 1, wherein the metering factor of the pump is calibrated in a metering step from a source container in which an impeller of the peristaltic pump rotates through at least one full revolution.

* * * * *